(12) United States Patent
Khachaturov et al.

(10) Patent No.: US 9,874,695 B2
(45) Date of Patent: Jan. 23, 2018

(54) OPTICAL FIBER TIP ATTACHMENT

(71) Applicant: LUMENIS LTD., Yokneam Ilit (IL)

(72) Inventors: Arkady Khachaturov, Haifa (IL);
Yacov Domankevitz, Zichron Yaacov (IL); Assaf Preiss, Yokneam Ilit (IL)

(73) Assignee: LUMENIS LTD., Yokneam Ilit (IL)

( * ) Notice: Subject to any disclaimer, the term of this patent is extended or adjusted under 35 U.S.C. 154(b) by 0 days.

(21) Appl. No.: 15/002,667

(22) Filed: Jan. 21, 2016

(65) Prior Publication Data

US 2016/0131841 A1 May 12, 2016

Related U.S. Application Data

(63) Continuation of application No. 14/411,656, filed as application No. PCT/IB2013/055402 on Jul. 1, 2013, now Pat. No. 9,304,260.

(60) Provisional application No. 61/667,025, filed on Jul. 2, 2012.

(51) Int. Cl.
| | |
|---|---|
| *G02B 6/26* | (2006.01) |
| *G02B 6/36* | (2006.01) |
| *A61B 18/22* | (2006.01) |
| *A61B 18/24* | (2006.01) |

(52) U.S. Cl.
CPC ............. *G02B 6/262* (2013.01); *A61B 18/22* (2013.01); *A61B 18/24* (2013.01); *G02B 6/3624* (2013.01); *A61B 2018/2205* (2013.01); *A61B 2018/2238* (2013.01); *A61B 2018/2266* (2013.01); *A61B 2018/2272* (2013.01); *A61B 2018/2288* (2013.01)

(58) Field of Classification Search
CPC ...... G02B 6/262; G02B 6/3624; A61B 18/22; A61B 18/24
See application file for complete search history.

(56) References Cited

U.S. PATENT DOCUMENTS

| | | | |
|---|---|---|---|
| 4,648,892 A | 3/1987 | Kittrell et al. | |
| 5,833,683 A | 11/1998 | Fuller | |
| 2002/0197048 A1 | 12/2002 | Tourne | |
| 2003/0174974 A1 | 9/2003 | Yasuda et al. | |
| 2007/0073281 A1* | 3/2007 | Johnson ................ | A61B 18/24 606/15 |
| 2011/0103748 A1 | 5/2011 | Ott | |
| 2011/0178509 A1 | 7/2011 | Zerfas et al. | |

* cited by examiner

*Primary Examiner* — Ryan Lepisto
(74) *Attorney, Agent, or Firm* — ISUS Intellectual Property PLL; A. Jason Mirabito (57) ABSTRACT

An optical fiber tip attachment comprising:
a body having an opening at a first end of the body, the opening configured to receive an optical fiber; and
a cavity extending from the opening through at least a portion of the body, wherein the cavity is configured to orient a cross-sectional surface of the optical fiber, from which electromagnetic radiation is delivered, at an angle to an axis of the optical fiber tip attachment at the opening.

6 Claims, 6 Drawing Sheets

OPTICAL FIBER TIP ATTACHMENT

RELATED APPLICATIONS

This Application is a continuation application of U.S. application Ser. No. 14/411,656, filed Dec. 29, 2014, now U.S. Pat. No. 9,304,260, granted on Apr. 5, 2016, which is a 371 national phase application of PCT/IB2013/055402, filed Jul. 1, 2013, which claims priority to U.S. Provisional Patent Application No. 61/667,025, filed Jul. 2, 2012.

BACKGROUND

Lasers are used in a variety of medical procedures, such as treatment of kidney stones and benign prostatic hyperplasia, for example. In some such medical procedures it is advantageous to utilize an optical fiber that delivers the laser or electromagnetic radiation at an angle rather than along the axis of the optical fiber. Such fibers are commonly referred to as side-firing lasers. Typical side-firing lasers use reflection, such as internal reflection, to direct the laser at an angle.

SUMMARY

According to a first aspect of the invention there is provided an optical fiber tip attachment comprising a body having an opening at a first end of the body, the opening configured to receive an optical fiber; and a cavity extending from the opening through at least a portion of the body, wherein the cavity is configured to orient a cross-sectional surface of the optical fiber, from which electromagnetic radiation is delivered, at an angle to an axis of the optical fiber tip attachment at the opening The optical fiber tip attachment may comprise a second opening, the cavity extending from the first opening to the second opening.

The cavity may be configured to orient a cross-sectional surface of the optical fiber at an angle to an axis that is perpendicular to a plane through the opening in the body.

The optical fiber tip attachment may further comprise a top located at a second end of the body.

The cavity may extend through a portion of the body and a portion of the top.

The cavity may extend only through the body.

The top may have a hemispherical shape.

The top and body may be formed from a single continuous material.

The top may be formed as a separate element from the body, the top being attached to the second end of the body.

The top may include at least one extension configured to be coupled to an inner surface of the body.

The cavity may have an approximately uniform width.

The cavity may comprised of a chamber and a channel, wherein the chamber is wider than the channel.

Where the optical fiber tip attachment comprises a top, the chamber may extend through the body and the channel may extend through the top.

Where the optical fiber tip attachment comprises a second opening, the chamber may be proximate the first opening and the channel may be proximate the second opening.

The cavity may be configured to orient the optical fiber such that the cross-sectional surface of the optical fiber is not perpendicular to an axis of the optical fiber when the optical fiber is cut to be approximately flush with an outer surface of the optical fiber tip attachment.

The cavity may be curved to orient the optical fiber.

An outer surface of the body and top may be curved, the curvature of the outer surface of the body and top corresponding to the curvature of the cavity.

The optical fiber tip attachment may be divided along a longitudinal axis into a first segment and a second segment, wherein the first segment may comprises a first half of the body and a first half of the cavity; and wherein the second segment may comprise a second half of the body and a second half of the cavity, the first and second segments being configured to be coupled together to secure the optical fiber in the cavity.

Where the optical fiber tip attachment comprises a top, the first segment may comprise a first half of the top and the second segment may comprise a second half of the top According to a second aspect of the invention there is provided an optical fiber assembly comprising an optical fiber having a bulbous portion at a first end of the optical fiber; and an optical fiber tip attachment according to the first aspect of the invention having a first end and a second end, the optical fiber tip attachment surrounding a segment of the optical fiber proximate the bulbous portion, the first end of the optical fiber tip attachment coupled to the bulbous portion, wherein the optical fiber tip attachment is configured to bend the segment of the optical fiber surrounded by the optical fiber tip attachment.

The optical fiber tip attachment may be further configured to maintain an air gap between a cylindrical surface of the segment of the optical fiber surrounded by the optical fiber tip attachment and an inner surface of the optical fiber tip attachment.

An outer surface and an inner surface of the optical fiber tip attachment may be curved longitudinally.

According to a third aspect of the invention there is provided a laser system comprising an optical fiber, a laser energy source configured to provide electromagnetic radiation to a first end of the optical fiber, and an optical fiber tip attachment coupled to a second end of the optical fiber, the optical fiber tip attachment comprising an optical fiber tip attachment according to the first aspect of the invention.

DRAWINGS

Understanding that the drawings depict only exemplary embodiments and are not therefore to be considered limiting in scope, the exemplary embodiments will be described with additional specificity and detail through the use of the accompanying drawings, in which.

In accordance with common practice, the various described features are not drawn to scale but are drawn to emphasize specific features relevant to the exemplary embodiments.

DETAILED DESCRIPTION

In the following detailed description, reference is made to the accompanying drawings that form a part hereof, and in which is shown by way of illustration specific illustrative embodiments. However, it is to be understood that other embodiments may be utilized and that logical, mechanical, and electrical changes may be made. The following detailed description is, therefore, not to be taken in a limiting sense.

Figure 1:
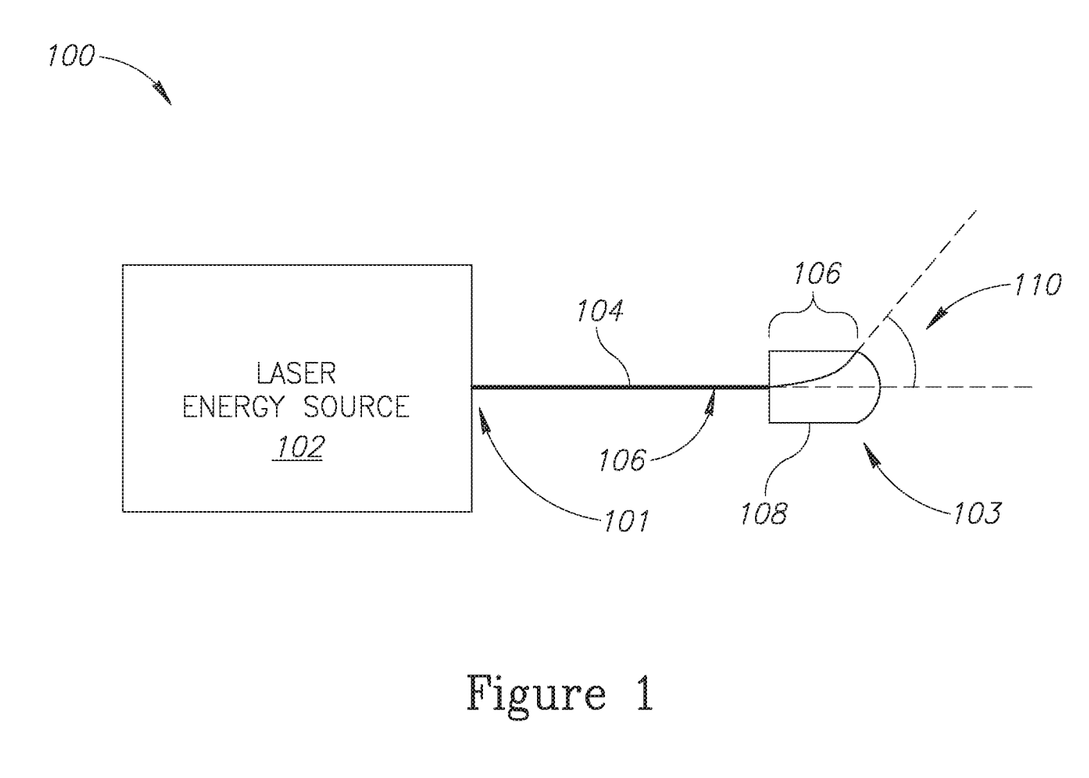
FIG. 1 is a high level block diagram of one embodiment of an exemplary laser system.

FIG. 1 is a high level block diagram of one embodiment of an exemplary laser system 100. System 100 includes a laser energy source 102 configured to provide electromagnetic radiation to an optical fiber 104. The optical fiber 104 has a first end 101 coupled to the optical fiber 104 for receiving the electromagnetic radiation generated by the laser energy source 102 and a second end 103 from which the electromagnetic radiation is delivered to a target. For example, the system 100 can be used in performing medical procedures that involve delivery of electromagnetic radiation to tissue, such as, but not limited to, medical procedures for treating benign prostatic hyperplasia (BPH).

The optical fiber 104 is comprised of a fiber core, cladding, and buffer or coating, as known to one of skill in the art. In a section 106 at the second end 103 of the optical fiber 104, the optical fiber 104 extends beyond an outer jacket or sheath 116 as shown in FIG. 1. In addition, a rigid fiber tip 108 (also referred to herein as a fiber tip or fiber tip attachment) is placed over the optical fiber 104 in section 106. The rigid fiber tip 108 is configured to cause the optical fiber to bend such that the electromagnetic radiation is delivered at an angle 110 from an axis 112 that is perpendicular to a cross-sectional surface of the outer jacket 116 as described in more detail below with respect to FIG. 2.

Figure 2:
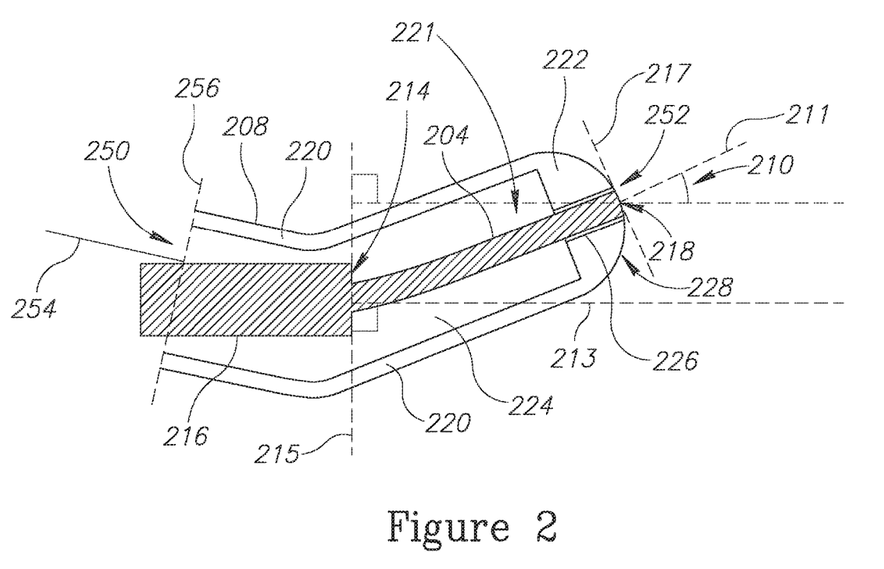
FIG. 2 is a cross-sectional view of one embodiment of an exemplary fiber tip attachment.

In particular, FIG. 2 depicts one exemplary embodiment of a fiber tip 208 for an optical fiber 204. As shown in FIG. 2, the orientation of the cross-sectional surface 214 of the outer jacket 216 is depicted by axis 213 which is perpendicular to the plane 215 that extends through the cross-sectional surface 214. Similarly, the orientation of a cross-sectional surface 218 of the optical fiber 204 is depicted by axis 211 which is perpendicular to the plane 217 that extends through the cross-sectional surface 218. The cross-sectional surface 218 is also referred to herein as an emission surface because the electromagnetic radiation is emitted through surface 218.

The body 220 and top 222 of the fiber tip 208 are comprised of a rigid material such as, but not limited to, metals, metal alloys, or rigid polymers. The body 220 is an elongated portion of the fiber tip 208 and the top 222 is a rounded portion at the end of the fiber tip 208. The fiber tip 208 includes a cavity 221 that extends from a first opening 250 in the fiber tip 208 to a second opening 252 in the fiber tip 208. In this embodiment, the cavity 221 extends through both the body 220 and top 222. It is to be understood that although the orientation of the surface 218 is described in relation to the orientation of the cross-sectional surface 214, the orientation of the surface 218 can also be described in relation to an orientation of the first opening 250. That is, the fiber tip 208 is configured to orient the surface 218 at an angle to an axis 254 that is perpendicular to a plane 256 through the first opening.

In addition, in this example, the cavity 221 includes a channel 226 formed through the top 222 and a chamber 224 formed through the body 220. The chamber 224 is placed over the exposed portion of the optical fiber 204 and a portion of the outer jacket 216. The body 220 is angled such that it contacts the outer jacket 216 to hold the fiber tip 208 in place.

As shown in FIG. 2, the width of the channel 226 is narrower than the width of the chamber 224. In particular, the width of the channel 226 is approximately equal to, but larger than, the diameter of the optical fiber 204 such that the optical fiber 204 is maintained inside the channel 226 through friction. Thus, a force can be applied to the optical fiber 204 to push the end of the optical fiber 204 beyond an outer surface 228 of the top 222. The optical fiber 204 can then be cut or cleaved such that the cross-sectional surface 218 is approximately flush with the outer surface 228. By enabling the cutting of the optical fiber 204, the fiber tip 208 enables damaged or degraded fiber at the end of the optical fiber to be removed and the remaining portion of the optical fiber 204 to continue to be used.

In addition, in the example of FIG. 2, the channel 226 is located approximately in the center of the top 222. However, since the body 220 is bent, the orientation of the cross-sectional surface 218 of the optical fiber 204 is displaced at an angle 210 from the orientation of the cross-sectional surface 214 of the outer jacket 216. The angle 210 is determined and configured based on the intended application or use of the optical fiber 204. For example, the rigid fiber tip 208 can be configured, in some embodiments, to displace the optical fiber 204 at an angle selected from the range of 75° to 90°.

Figure 3:
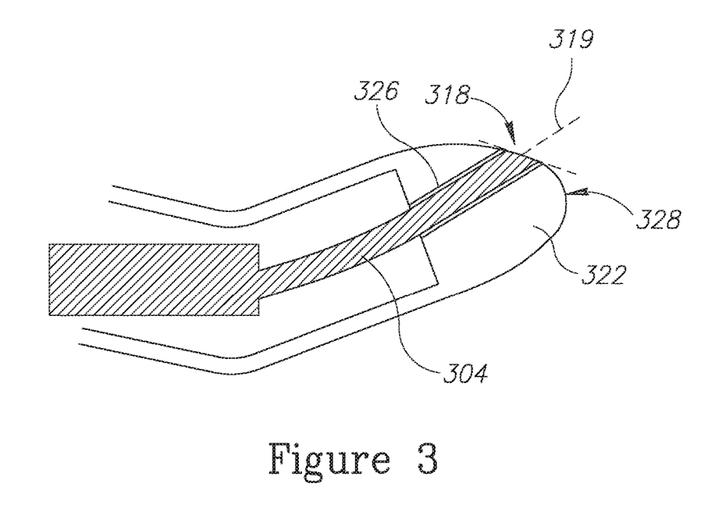
FIG. 3 is a cross-sectional view of another embodiment of an exemplary fiber tip attachment.

Although the top 222 has a hemispherical shape in the example of FIG. 2, it is to be understood that other shapes can be used in other embodiments. For example, in FIG. 3, the top 322 has an elongated irregular shape approximately in the form of a semi-elliptical shape. Also, the channel 326 in FIG. 3 is located off-center. That is, the channel 326 is not located in approximately the center of the top 322. Furthermore, as shown in FIG. 3, due to the shape of the top 322 and the location of the channel 326, the surface 318 of the optical fiber 304 is not perpendicular to the fiber axis 319 when cut to be approximately flush with the outer surface 328 of the top 322. The axis 319 is a longitudinal axis of the fiber 304 at the second opening The angled surface 318, thus, influences the direction of electromagnetic radiation that is delivered from the tip of the optical fiber 304. Therefore, the shape of the top 322 and location of the channel 326 can be configured to determine the angle at which the electromagnetic radiation is delivered.

Figure 4:
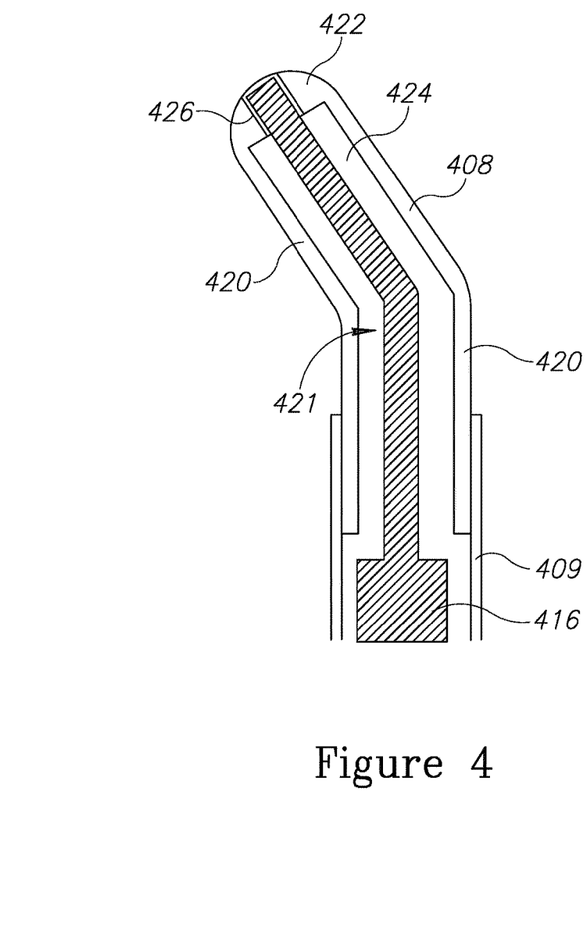
FIG. 4 is a cross-sectional view of another embodiment of an exemplary fiber tip attachment.

FIG. 4 depicts a cross-sectional view of another embodiment of an exemplary rigid fiber tip 408. Similar to fiber tip 208, fiber tip 408 includes a cavity 421 including a chamber 424, defined by body 420 and top 422, and a channel 426 in the top 422. In addition, fiber tip 408 depicts an alternative technique for attaching the fiber tip 408 to the optical fiber 404 and outer jacket 416. In particular, the fiber tip 408 is inserted into and attaches to a rigid sheath 409 having dimensions that enable the sheath 409 to fit over and attach to the outer jacket 416 rather than using the configuration of the body 420 to hold the fiber tip 408 in place.

Furthermore, it is to be understood that in other embodiments, the fiber tip is configured differently. For example, the exemplary fiber tip 508 shown in FIGS. 5A and 5B does not curve as in the exemplary fiber tips discussed above.

Figure 5A:
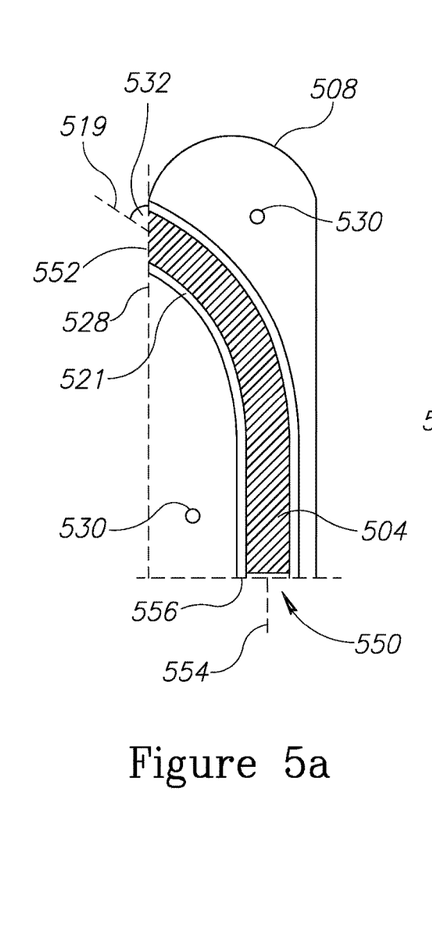
FIG. 5A is a cross-sectional view of another embodiment of an exemplary fiber tip attachment.
Figure 5B:
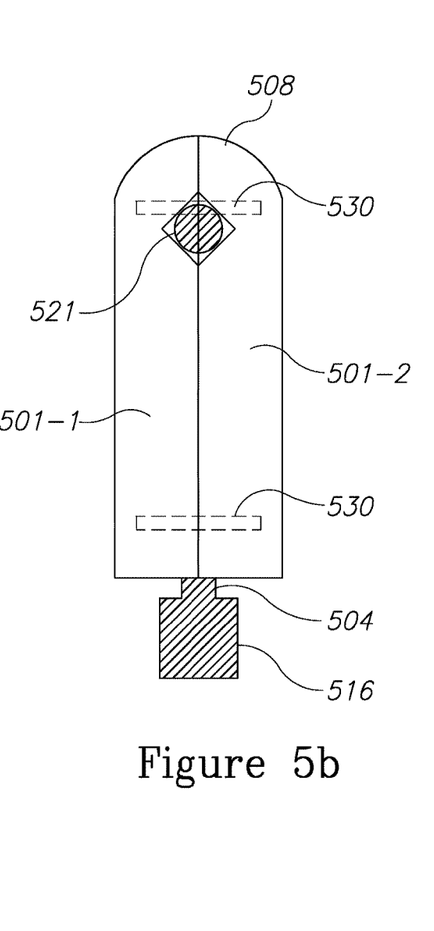
FIG. 5B is a front view of the exemplary fiber tip attachment of FIG. 5A.

Additionally, as shown in the cross-section side view in FIG. 5A, the cavity 520 of fiber tip 508 does not include a hollow chamber and a channel Rather, the cavity 521 has a substantial uniform width as it extends through the fiber tip 508. A fiber optic cable 504 is placed in the cavity 521. In particular, as shown in FIG. 5B, the fiber tip 508 is comprised of two corresponding sections 501-1 and 501-2. Each section contains a cavity 521 which matches the cavity 521 in the other section. After placing a fiber optic cable 504 into the cavity 521 of one of the sections 501, the two sections 501-1 and 501-2 are coupled together, such as with screws 530. Once coupled together, the sections 501-1 and 501-2 form the complete cavity 521. The size of the cavity 521 is approximately equal to, but larger than, the diameter of the optical fiber 504 such that the optical fiber 504 is maintained in place in the cavity 521 via the force of friction. Also, since the cavity 521 maintains the optical fiber 504 in position, the fiber tip 508 does not need to be directly attached to the outer jacket 516, as shown in FIG. 5.

In addition, although the fiber tip 508 is not curved, the cavity 521 is curved such that the emission surface 518 of the fiber 504 is oriented at an angle to the axis 554 which is perpendicular to a plane 556 through the opening 550 of the fiber tip 508. Similar to the exemplary fiber tip shown in FIG. 3, the location and orientation of the cavity 521 in the fiber tip 508 causes the optical fiber to be cut an angle 532 that is not perpendicular to the axis 519 of the optical fiber 504 at the second opening 552 when the fiber 504 is cut to be approximately flush with an outer surface 528 of the fiber tip 508.

Figure 6:
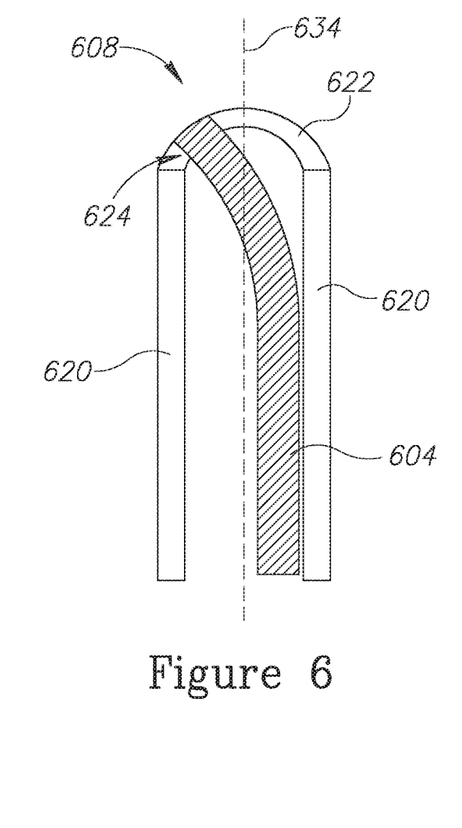
FIG. 6 is a cross-sectional view of another embodiment of an exemplary fiber tip attachment.
Figures 7, 8:
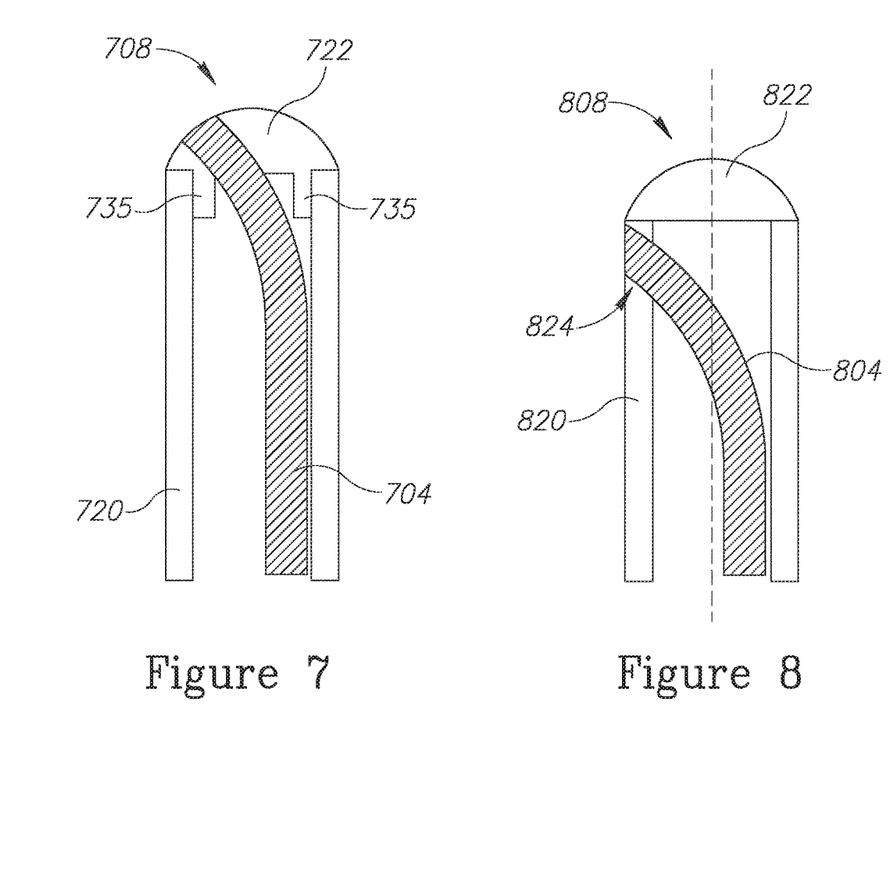
FIG. 7 is a cross-sectional view of another embodiment of an exemplary fiber tip attachment.
FIG. 8 is a cross-sectional view of another embodiment of an exemplary fiber tip attachment.

Other configurations of the fiber tip are also implemented in other embodiments. For example, FIGS. 6-8 depict exemplary configurations of the body, top, and cavity of a fiber tip. In particular, in FIG. 6, the body 620 and top 622 are not formed integrally as one continuous material. Rather the top 622 is a separate element that is coupled to the body 620. In addition, the top 622 is shaped as a hollow hemisphere with the channel 624 formed through the top 622 at an angle to the longitudinal axis 634 of the fiber tip 608.

In FIG. 7, the top 722 and the body 720 are also separate elements as in the example of FIG. 6. However, the top 722 is a hemispherical shape with extensions 735. The extensions 735 support the attachment of the top 722 to the body 720. In the example of FIG. 8, the top 822 is also hemispherical in shape. However, in the example of FIG. 8, the channel 824 of the cavity 821 is formed in the body 820 rather than the top 822.

Figure 9:
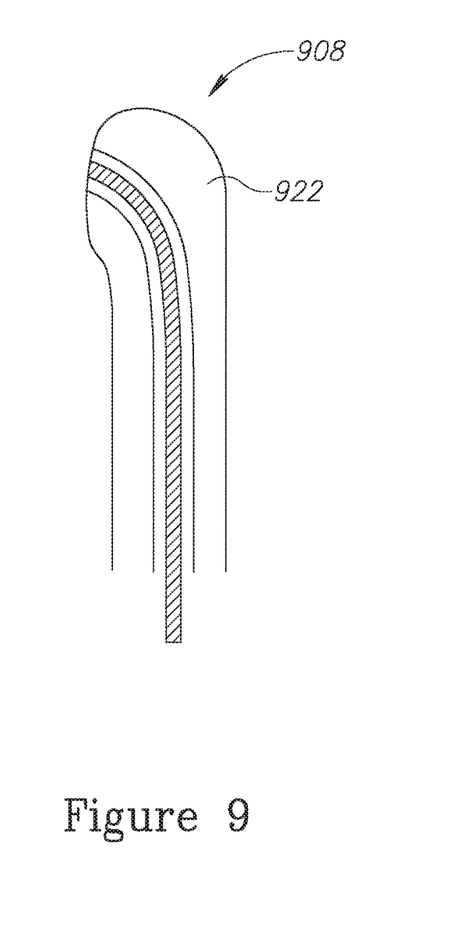
FIG. 9 is a cross-sectional view of another embodiment of an exemplary fiber tip attachment.
Figure 10:
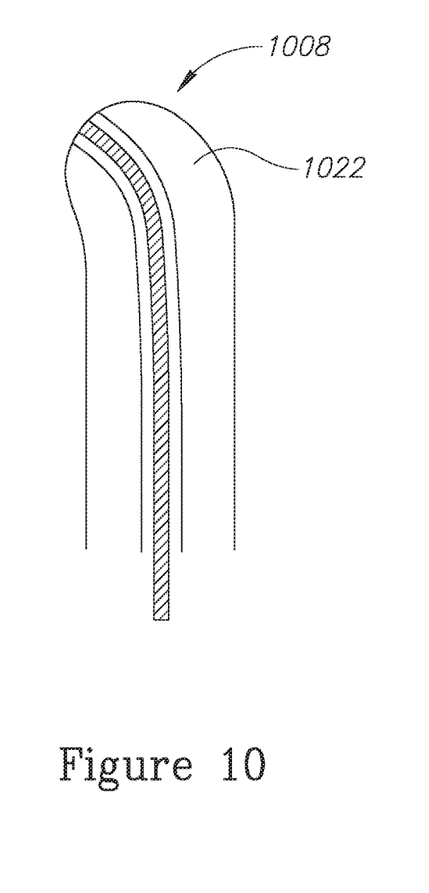
FIG. 10 is a cross-sectional view of another embodiment of an exemplary fiber tip attachment.
Figure 11:
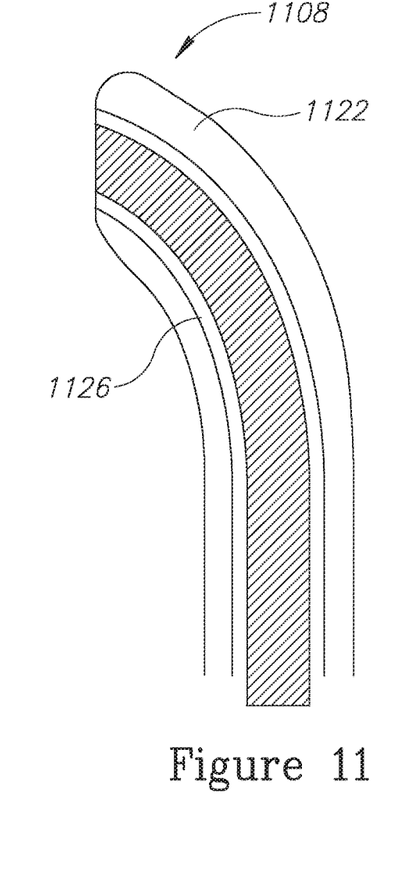
FIG. 11 is a cross-sectional view of another embodiment of an exemplary fiber tip attachment.

FIGS. 9-11 depict other exemplary configurations of the fiber tip. In particular, in the examples shown in FIGS. 9-11, the body and top are formed integrally as one continuous material. As shown in FIGS. 9-11, the respective fiber tips 908, 1008, and 1108 vary in shape from one another. For example, the top 1022 of fiber tip 1008 is more spherical than the top 922 or 1122, whereas, the shape of fiber tip 1108 mirrors more closely the path of the channel 1126. In addition, the fiber tip does not have to be made of straight segments which are bent at an angle. Indeed, the outer surface and inner surface of the exemplary fiber tips in FIGS. 9-11 are gradually curved longitudinally. That is, the fiber tips curve along the length of the fiber tip. Hence, it is to be understood that the shape of the fiber tip, as well as the placement of the channel can change depending on the specific implementation.

Figure 12:
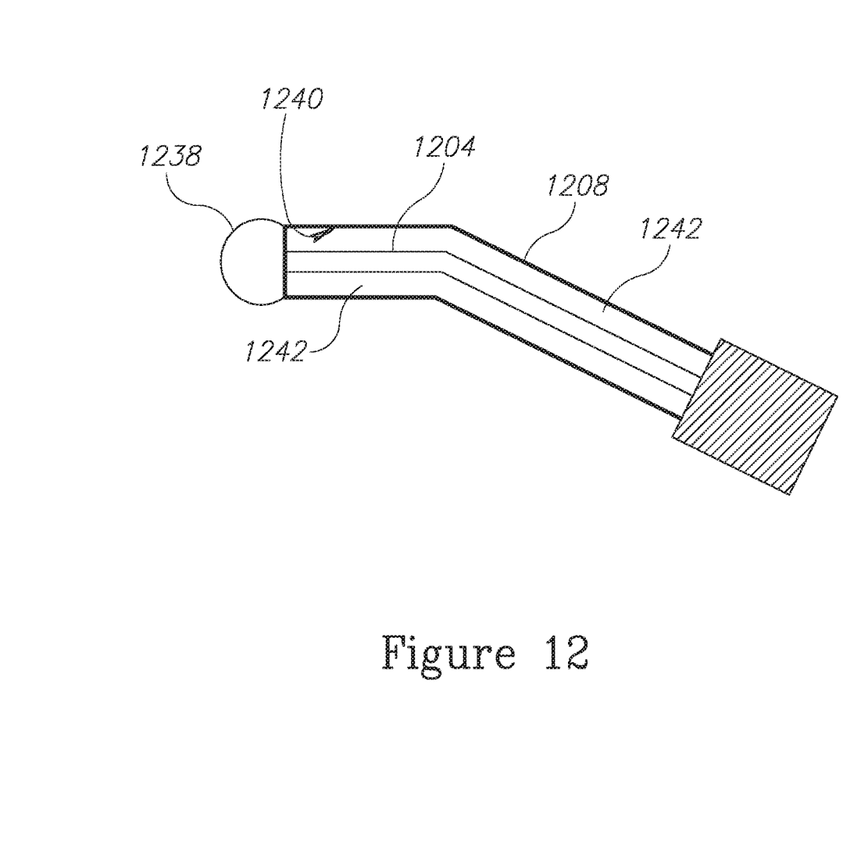
FIG. 12 is a cross-sectional view of another embodiment of an exemplary fiber tip attachment.
Figure 13:
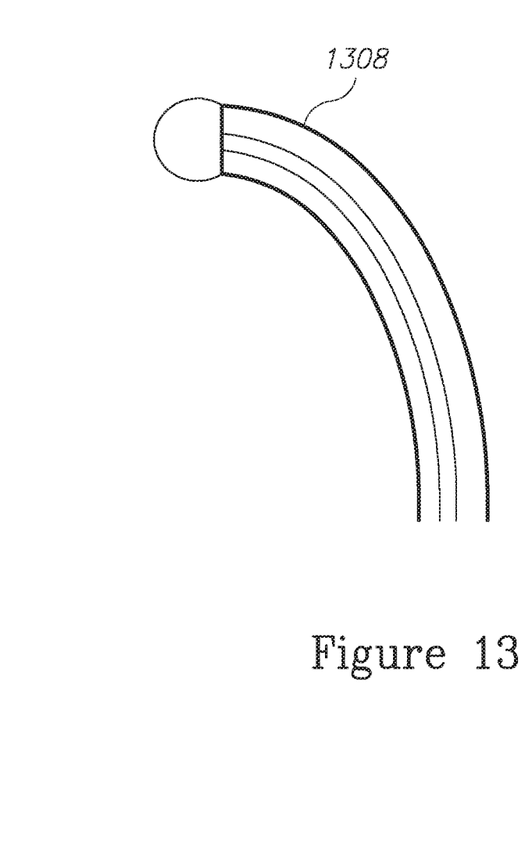
FIG. 13 is a cross-sectional view of another embodiment of an exemplary fiber tip attachment.

For example, the shape of the fiber tip can be configured for optical fibers having irregular shapes, such as the optical fiber 1204 in FIG. 12. The optical fiber 1204 includes a bulbous portion 1238 at the end of the optical fiber 1204. The fiber tip 1208 attaches to the base of the bulbous portion 1238 via an adhesive, for example. In addition, the fiber tip 1208 is rigid and provides a gap 1242 between the optical fiber 1204 and an inner surface 1240 of the fiber tip 1208. The gap 1242 helps prevent leakage of the electromagnetic radiation from the optical fiber 1204 into the surrounding environment, such as tissue. The rigid fiber tip 1208 is also bent to cause the optical fiber 1204 to bend as described above. Fiber tip 1308 is similar to fiber tip 1208. However, rather than being bent at an angle like fiber tip 1208, the fiber tip 1308 is curved longitudinally.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

The invention claimed is:

1. An optical fiber assembly comprising:
    an optical fiber having a first, distal end and a second, proximal end;
    an outer jacket surrounding the optical fiber except at the first distal end;
    an optical fiber tip attachment attached to the distal end of the optical fiber having an elongated cylindrically-shaped body including a tip portion having a hemispherical shape and one or more side walls proximal of the tip portion with an opening at a first proximal end of the body, the proximal opening configured to receive the distal end of the optical fiber;
    a second opening in one of the one or more sidewalls of the elongated cylindrically-shaped body portion proximal of the hemispherically-shaped tip portion;
    a cavity extending from the first proximal opening through the body to the second opening, the cavity being sized to receive the distal end of the optical fiber and shaped such that the cavity bends and opens into the second opening, wherein the cavity receives and bends an optical fiber inserted into the cavity;
    the cavity along its entire extent from the first proximal opening through the body to the second opening having an inside diameter approximately equal to but greater than the outside diameter of an optical fiber inserted in the cavity; and,
    wherein the distal end of the optical fiber is positioned within the cavity and secured from movement by frictional engagement of the outside of the optical fiber with the inside of the cavity and wherein the outer jacket is outside of the first proximal opening.

2. The optical fiber assembly of claim 1 further comprising a laser energy source configured to provide electromagnetic radiation from the proximal end of the optical fiber through and out the distal end of the optical fiber.

3. The optical fiber assembly of claim 1 wherein optical fiber may be moved by applying a force to the proximal end of the optical fiber to overcome the frictional engagement of the optical fiber in the channel.

4. An optical fiber assembly comprising:
an optical fiber tip attachment for attachment to the distal end of an optical fiber having an elongated cylindrically-shaped body including a tip portion having a hemispherical shape and one or more side walls proximal of the tip portion with an opening at a first proximal end of the body, the proximal opening configured to receive a distal end of an optical fiber;
a second opening in one of the one or more side walls of the elongated cylindrically-shaped body portion proximal of the hemispherically-shaped tip portion;
a cavity extending from the first proximal opening through the body to the second opening, the cavity being sized to receive the distal end of an optical fiber and shaped such that the cavity bends and opens into the second opening;
wherein the cavity receives and bends an optical fiber inserted into the cavity;
the cavity having an inside diameter along its entire extent from the first proximal opening through the body to the second opening approximately equal to but greater than the outside diameter of an optical fiber inserted in the cavity; and,
wherein an optical fiber tip when positioned within the cavity is secured from movement by frictional engagement of the outside of the optical fiber with the inside of the cavity.

5. The optical fiber assembly of claim 4 further comprising a laser energy source configured to provide electromagnetic radiation from the proximal end of the optical fiber through and out the distal end of the optical fiber.

6. The optical fiber assembly of claim 4 wherein the optical fiber may be moved by applying a force to the proximal end of the optical fiber to overcome the frictional engagement of the optical fiber in the channel.

* * * * *